(12) United States Patent
Rezach et al.

(10) Patent No.: US 8,668,724 B2
(45) Date of Patent: Mar. 11, 2014

(54) GROMMET ASSEMBLY

(75) Inventors: Alan Rezach, Cordova, TN (US); Matthew M. Morrison, Cordova, TN (US); Terry Sites, North Manchester, IN (US); Joshua Beery, North Manchester, IN (US); B. Thomas Barker, Bartlett, TN (US); Harold S. Taylor, Memphis, TN (US); Ryan E. Schumacher, Warsaw, IN (US)

(73) Assignee: Warsaw Orthopedic, Inc, Warsaw, IN (US)

(*) Notice: Subject to any disclaimer, the term of this patent is extended or adjusted under 35 U.S.C. 154(b) by 1119 days.

(21) Appl. No.: 11/845,477

(22) Filed: Aug. 27, 2007

(65) Prior Publication Data

US 2007/0293861 A1    Dec. 20, 2007

Related U.S. Application Data

(62) Division of application No. 10/720,771, filed on Nov. 24, 2003, now Pat. No. 7,261,715.

(51) Int. Cl.
*A61B 17/70*    (2006.01)

(52) U.S. Cl.
USPC .......................................... 606/303; 606/267

(58) Field of Classification Search
USPC ........................... 24/625; 403/326, 329, 385; 606/246–279, 303, 324, 914
IPC ....................................................... A61B 17/70
See application file for complete search history.

(56) References Cited

U.S. PATENT DOCUMENTS

| | | | |
|---|---|---|---|
| 2,940,783 A | 6/1960 | Englehardt | |
| 4,483,334 A | 11/1984 | Murray | |
| 4,569,338 A | 2/1986 | Edwards | |
| 4,718,151 A | 1/1988 | LeVahn et al. | |
| 4,805,602 A * | 2/1989 | Puno et al. | 606/267 |
| 4,827,918 A | 5/1989 | Olerud | |
| 4,946,122 A | 8/1990 | Ramsey et al. | |
| 4,987,892 A | 1/1991 | Krag | |
| 5,002,542 A | 3/1991 | Frigg | |
| 5,047,029 A | 9/1991 | Aebi et al. | |
| 5,053,034 A | 10/1991 | Olerud | |
| 5,122,131 A * | 6/1992 | Tsou | 606/328 |
| 5,254,118 A | 10/1993 | Mirkovic | |
| 5,261,909 A | 11/1993 | Sutterlin et al. | |
| 5,344,422 A | 9/1994 | Frigg | |
| 5,352,226 A | 10/1994 | Lin | |
| 5,380,323 A | 1/1995 | Howland | |
| 5,527,314 A * | 6/1996 | Brumfield et al. | 606/278 |

(Continued)

FOREIGN PATENT DOCUMENTS

| | | |
|---|---|---|
| EP | 0 553424 | 11/1992 |
| EP | 0 786 235 B1 | 1/1997 |

(Continued)

*Primary Examiner* — Pedro Philogene
*Assistant Examiner* — Lynnsy Schneider (57) ABSTRACT

A connecting device is provided for use in orthopedic surgery, for example to connect a spinal rod and a vertebral screw or hook. The connector generally includes a receiver member for receiving an elongated member, and a grommet member for receiving a bone fixation member. The grommet member is inserted into the receiver member so that the receiver member and grommet member are rotatably connected. One or more disks may be placed between the receiver member and grommet member to assist in locking the device.

17 Claims, 6 Drawing Sheets

(56) References Cited

U.S. PATENT DOCUMENTS

| | | | |
|---|---|---|---|
| 5,534,002 A | 7/1996 | Brumfield et al. | |
| 5,540,688 A * | 7/1996 | Navas | 606/266 |
| 5,562,662 A | 10/1996 | Brumfield et al. | |
| 5,584,831 A | 12/1996 | McKay | |
| 5,591,165 A | 1/1997 | Jackson | |
| 5,613,968 A * | 3/1997 | Lin | 606/320 |
| 5,624,440 A | 4/1997 | Huebner | |
| 5,634,925 A | 6/1997 | Urbanski | |
| 5,643,263 A | 7/1997 | Simonson | |
| 5,643,264 A | 7/1997 | Sherman et al. | |
| 5,645,544 A | 7/1997 | Tai et al. | |
| 5,709,685 A | 1/1998 | Dombrowski et al. | |
| 5,810,816 A | 9/1998 | Roussouly et al. | |
| 5,879,351 A | 3/1999 | Viart | |
| 5,885,285 A * | 3/1999 | Simonson | 606/278 |
| 5,938,663 A | 8/1999 | Petreto | |
| 5,947,965 A | 9/1999 | Bryan | |
| 5,947,967 A | 9/1999 | Barker | |
| 5,976,135 A | 11/1999 | Sherman et al. | |
| 5,980,521 A * | 11/1999 | Montague et al. | 606/252 |
| 6,027,533 A | 2/2000 | Olerud | |
| 6,030,388 A | 2/2000 | Yoshimi et al. | |
| 6,083,226 A | 7/2000 | Fiz | |
| 6,086,588 A | 7/2000 | Ameil et al. | |
| 6,106,526 A | 8/2000 | Harms et al. | |
| 6,123,706 A | 9/2000 | Lange | |
| 6,183,473 B1 | 2/2001 | Ashman | |
| 6,187,005 B1 | 2/2001 | Brace et al. | |
| 6,210,413 B1 | 4/2001 | Justis et al. | |
| 6,248,107 B1 | 6/2001 | Foley et al. | |
| 6,371,957 B1 | 4/2002 | Amrein et al. | |
| 6,402,749 B1 | 6/2002 | Ashman | |
| 6,471,703 B1 | 10/2002 | Ashman | |
| 6,520,962 B1 * | 2/2003 | Taylor et al. | 606/278 |
| 6,547,789 B1 * | 4/2003 | Ventre et al. | 606/308 |
| 6,554,834 B1 * | 4/2003 | Crozet et al. | 606/65 |
| 6,562,038 B1 | 5/2003 | Morrison | |
| 6,579,292 B2 * | 6/2003 | Taylor | 606/278 |
| 6,685,705 B1 | 2/2004 | Taylor | |
| 6,810,880 B1 * | 11/2004 | Jennings et al. | 128/849 |
| 6,832,999 B2 | 12/2004 | Ueyama et al. | |
| RE39,035 E * | 3/2006 | Finn et al. | 606/264 |
| 2002/0156476 A1 * | 10/2002 | Wilford | 606/72 |
| 2002/0193794 A1 * | 12/2002 | Taylor | 606/61 |
| 2004/0010253 A1 | 1/2004 | Morrison | |
| 2004/0133203 A1 * | 7/2004 | Young et al. | 606/61 |

FOREIGN PATENT DOCUMENTS

| | | |
|---|---|---|
| EP | 0 786 235 A2 | 7/1997 |
| EP | 0 982 007 A2 | 3/2000 |
| FR | 2 692 471 A1 | 12/1993 |
| FR | 2 806 902 A1 | 10/2001 |
| WO | WO 01/67972 A3 | 9/2001 |
| WO | WO 02/47564 A2 | 6/2002 |

* cited by examiner

GROMMET ASSEMBLY

CROSS-REFERENCE TO RELATED APPLICATIONS

This application is a divisional of U.S. Ser. No. 10/720,771, filed Nov. 24, 2003, and priority and the benefit of Ser. No. 10/720,771 are claimed in the present application to the extent the subject matter of this application is found in the previously filed application. The content of that application is incorporated herein by reference.

FIELD OF THE INVENTION

This invention concerns devices used in orthopedic implants. More particularly, this invention concerns connectors between parts of an orthopedic implant, such as an orthopedic rod and an elongated screw.

BACKGROUND OF THE INVENTION

There are a variety of known devices for connecting various parts of an orthopedic implant together. Among these are included connectors featured with TSRH-3D products of Medtronic Sofamor Danek, Inc. Such devices commonly include a part for holding an elongated member, such as a spinal rod, and a second member for holding a bone fixation element, such as a pedicle screw or hook. The two parts are connected together, preferably with the ability to rotate with respect to each other. Such devices are shown, for example, in U.S. Pat. No. 6,183,473 to Ashman and U.S. Pat. No. 5,643,263 to Simonson.

SUMMARY OF THE INVENTION

In one embodiment, an apparatus includes a receiver member having a channel therethrough, at least one aperture for a closure member, and an opening transverse to the channel, and a grommet member having a passage therethrough and a transverse extension, wherein the extension is inserted through the transverse opening of the receiver member so that the grommet member is rotatably connected to the receiver member. The extension can be compressible, and/or can include at least one prong. In an embodiment having at least two prongs, a clip can be positioned between the prongs. The extension may have a groove to accommodate a portion of a retaining ring or one or more retaining pins. The receiver member may include an internal countersunk portion defining a ledge, which ledge can be integral or a part of an insert connected to the receiver member. One or more intermediate members, such as disks, can be placed between the receiver member and the grommet member.

In another embodiment, an apparatus includes a receiver member having a body portion with a channel for accommodating a part of an elongated member and at least one opening for locking member, as well as an extension portion extending from the body portion substantially transversely to the channel. The extension portion has a hole therethrough communicating with the channel. A generally U-shaped grommet member having at least two prongs and a passage for accommodating a part of a bone fixation member is provided, with the prongs being inserted into the hole through the extension portion of the receiver member so that the grommet member is rotatably connected to the receiver member. A fixing member is lodged between at least two of the prongs, whereby the grommet member is prevented from being removed from the receiver member. First and second disks are also provided connected respectively to the receiver member and the grommet member and adjacent each other. The first disk has a first surface with a groove for contacting the elongated member and a second surface having radial splines. The second disk has a first surface having a groove for contacting the bone fixation member and a second surface having radial splines. The second surfaces of the first and second disk face each other.

Other embodiments are considered to be within the scope of the present invention.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Figure 1:
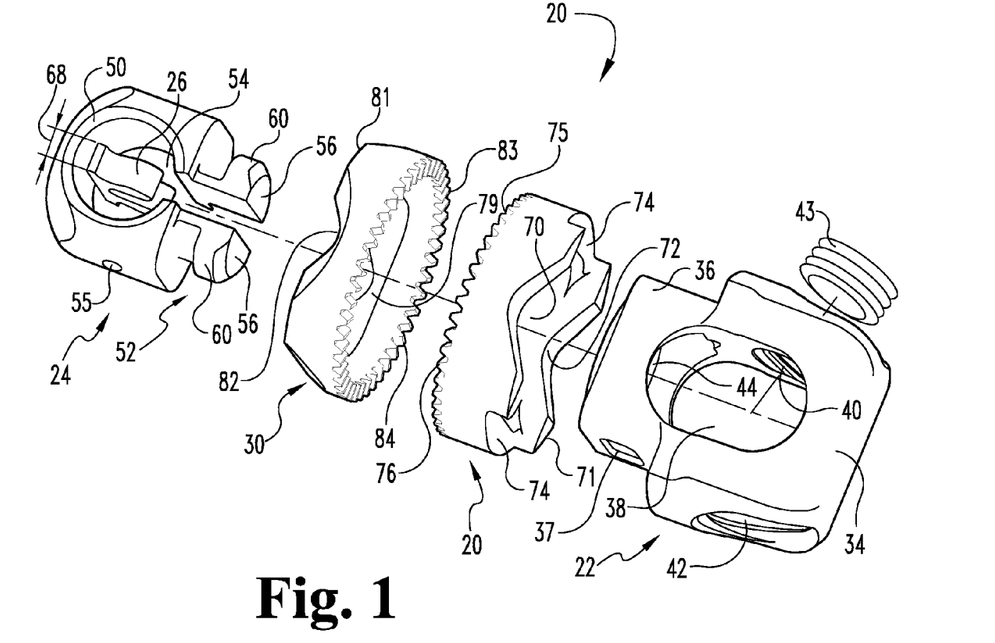
FIG. 1 is an exploded perspective view of one embodiment of an apparatus according to the present invention.
Figure 2:
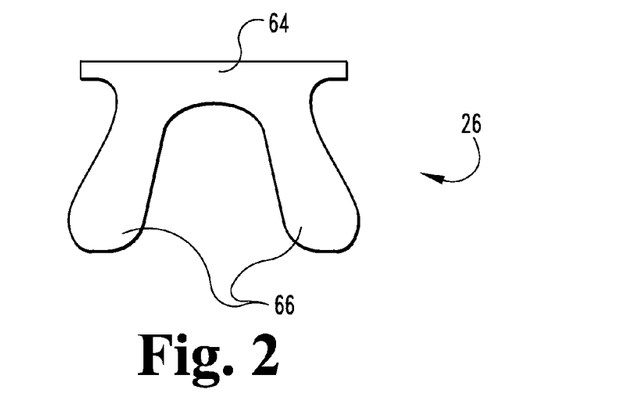
FIG. 2 is a front view of one embodiment of a clip useful in connection with the embodiment shown in FIG. 1.
Figure 3:
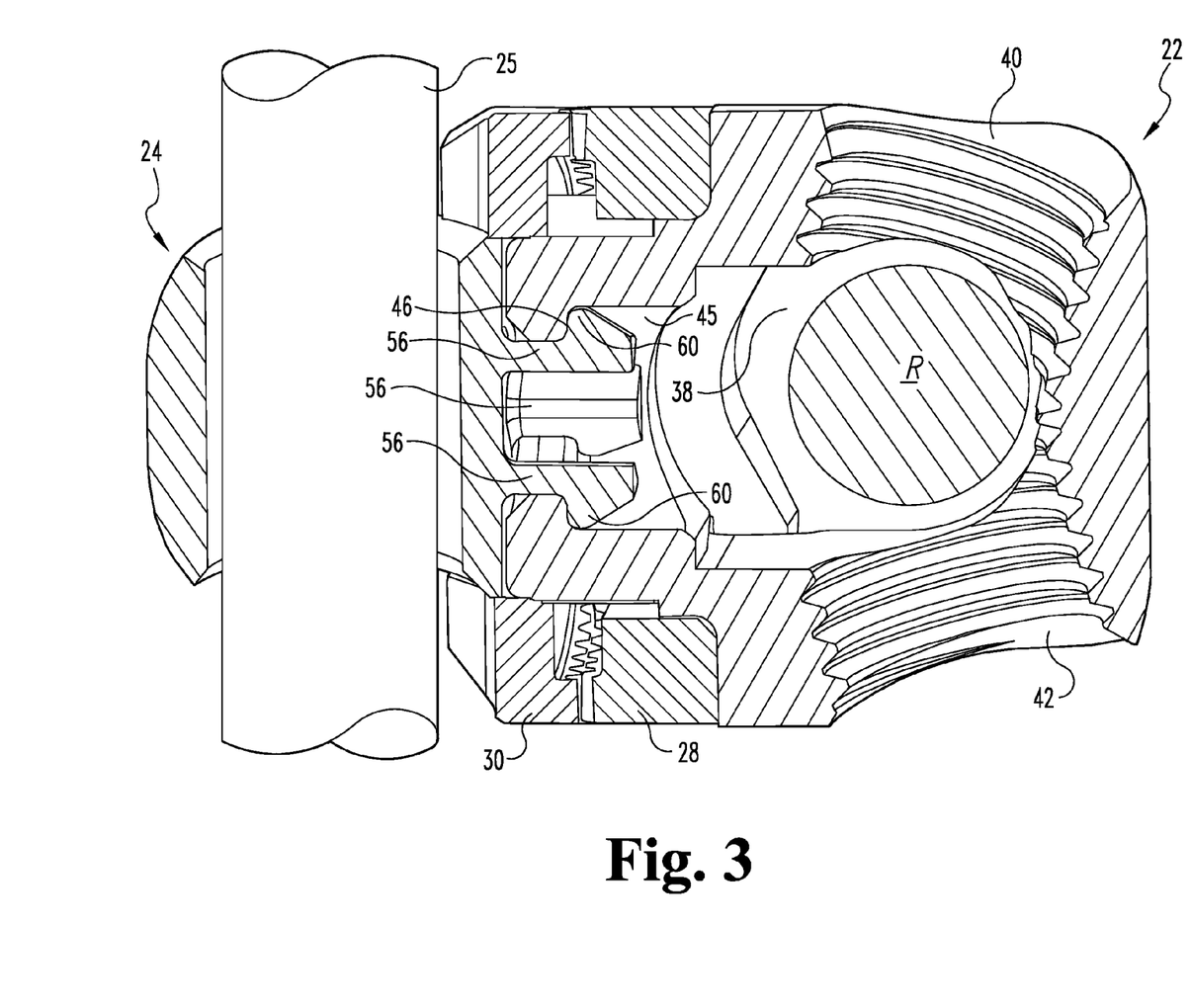
FIG. 3 is a cross-sectional view of the assembled embodiment of the apparatus depicted in FIG. 1, but without the embodiment of the clip shown in FIG. 2.

Referring generally to FIGS. 1-3, embodiments of a connector 20 are shown. Connector 20 generally includes a receiver member 22, and a grommet member 24. A fixing member 26 can be provided for interacting with grommet member 24, as will be discussed below. In a specific embodiment, disks 28 and/or 30 can also be provided, and if present are generally between receiver member 22 and grommet member 24. As will be described further below, receiver member 22 is designed to accommodate at least a part of an elongated member, such as spinal rod R, and grommet member 24 is designed to accommodate at least a part of a bone fixation member, such as a shank 25 of a pedicle or other orthopedic screw, hook, bolt or similar device. Shank 25 could also be a part of or connected to other implant items such as a connector, clamp or other device.

Receiver member 22, in one embodiment, includes a body portion 34 and an extension portion 36. Extension portion 36 can include one or more indentations or pockets 37, which in the illustrated embodiment are milled in an oval or elongated shape. An elongated aperture 38 extends through receiver member 22, and is sized to accommodate at least a portion of an elongated member. Holes 40 and 42 are provided in body portion 34 for a locking member. In the illustrated embodiment, holes 40 and 42 are threaded, and each is adapted to accommodate a set screw 43, to be threaded in and locked against an elongated member (e.g. rod R) within channel 38. The surgeon can use either of holes 40 and 42 for a locking member such as set screw 43, whichever may offer a more convenient access. Alternatively, both of holes 40 and 42 may be used by a surgeon to lock connector 20. It will be appreciated that only a single hole (e.g. hole 40 or hole 42) may be provided in another embodiment. A hole 44 is provided in extension portion 36, with hole 44 being substantially transverse to channel 38. Hole 44 includes a countersunk region 45 defining a ledge 46.

Grommet member 24 includes a body portion 50 and an extending grommet portion 52. Body portion 50 has a passage 54 therethrough for accommodating at least a portion of a bone anchor or fixation member, such as a shank 25 of a bone screw, a bone hook, a bone bolt or other anchoring member. Body portion 50 also may include one or more protrusions 55 extending from one or more side surfaces. In the embodiment shown in FIG. 1, grommet portion 52 includes two prongs 56, which attach to body portion 50 so that grommet member 24 is substantially U-shaped. In the embodiment shown in FIG. 3, grommet portion 52 includes four prongs 56 (one of which is not shown in the cross-sectional view of FIG. 3), each spaced about ninety degrees from two adjacent prongs 56.

Each of prongs 56 have a flange 60 that extends generally laterally to its respective prong 56. Flanges 60, taken together, have an outer diameter when grommet member 24 is unstressed (i.e. when prongs 56 are not being subjected to forces tending to move prongs 56 toward or away from each other) that is slightly larger than the inner diameter of hole 44, but is slightly smaller than the countersunk region 45 associated with hole 44. It will be seen that grommet portion 24 can be otherwise constructed, such as by providing a spring-loaded or biased member or shape-memory member in place of or in addition to prongs 56. Such a biased member could be C-shaped, substantially circular, or of other appropriate shape.

Grommet member 24 is connected to receiver member 22 by inserting extension portion 52 (prongs 56 in the embodiment of FIGS. 1 and 3) into hole 44. Prongs 56 in that embodiment can be squeezed together either by external pressure directly applied by an assembler, or by the action of hole 44 on flanges 60. Grommet member 24 can resume its unstressed form when flanges 60 move past ledge 46, e.g. prongs 56 of grommet member 24 snap into place with respect to receiver member 22. Grommet member 24 thus may snap-fit within receiver member 22 so that it is rotatably connected to receiver member 22. Preferably, one or more of flanges 60 cannot move past ledge 46 without pressing one or more of prongs 56 toward each other.

For embodiments of grommet member 24 having separate prongs 56, grommet member 24 can be locked within receiver member 22 by way of a fixing member 26, shown in FIG. 2 as a clip. Clip 26 is shown having a base portion 64 and two extending lobes 66. After grommet member 24 has been inserted within receiver member 22 as described above, and grommet member 24 has resumed its unstressed form, clip 26 can be inserted between prongs 56 of grommet member 24. Clip 26 occupies some or all of the space between prongs 56 to block the ability of prongs 56 to move toward each other, thus inhibiting or preventing removal of grommet member 24 from receiver member 22. Clip 26, in one embodiment, may have a width 68 (FIG. 1) that is approximately equal to or slightly larger than the gap between prongs 56 when prongs 56 and grommet portion 52 is in its unstressed state. If clip 26 is removed from between prongs 56, grommet member 24 can be compressed, so that the outer dimension of prongs 56 (and their extensions 60, if any) is smaller than the diameter of hole 44, and thus extension portion 52 of grommet member 24 can be removed from receiver member 22. For example, if grommet member 24 and receiver member 22 are subjected to stress tending to move them apart, then the edges of hole 44 could act on prongs 56 tending to force them together.

Alternatively, a fixing member 26 could comprise a block, such as a ball, cylinder, planar solid or other relatively solid structure. For example, with reference to the embodiment of FIG. 3, a ball having a diameter approximately the same as the distance between two non-adjacent prongs 56 can be placed or pressed into the center area surrounded by prongs 56. In this way, the ball effectively limits or prevents prongs 56 from moving toward each other, and grommet member 24 is maintained within receiver member 22. As another example, a cylinder or block could be placed or pressed endwise or lengthwise between prongs 56 of the embodiment of FIG. 1, or in the center area surrounded by prongs 56 of the embodiment of FIG. 3. If necessary or desired, an adhesive or other substance or agent, such as a bead or other formation of silicone, can be placed over or around the ball, cylinder, block or other fixing member and adjacent or between one or more of prongs 56 to maintain the clip, block or other fixing member in place. Fixing member 26, whether in the form of a clip, block or other structure, can be made of a shape-memory material, such as the nickel-titanium alloy known as NITINOL®, that can assume a fixing shape or size during or after implantation of grommet member 24 and receiver member 22.

In specific embodiments, one or more washers, disks or other intermediate members may be provided adjacent or around receiver member 22 and/or grommet member 24, and substantially between channel 38 in receiver member 22 and passage 54 in grommet member 24. As shown generally in the embodiment of FIG. 1, examples of disks 28 and 30 are illustrated. Disk 28 in this embodiment is associated with receiver member 22. Disk 28 has a substantially cylindrical exterior, although it may be of any of a variety of shapes or configurations, and has a hole 70 therethrough to accommodate at least a portion of extension portion 36 of receiver member 22. In a particular embodiment, hole 70 and extension portion 36 may be keyed together or both may have a similarly dimensioned square, rectangular, polygonal, rounded, tapered or other shape to ease the fitting together of receiver member 22 and disk 28, and/or to limit or prevent rotation with respect to each other.

On a first side 71 of disk 28, a channel 72 is formed. Channel 72 may have a portion that is approximately the same diameter as a spinal rod in channel 38, or may have a V-shaped cross section or other configuration. On that same side 71, disk 28 may further include one or more lateral openings 74 to accommodate a portion of body portion 34 of receiver member 22. Thus, when disk 28 is in use, it can slide onto extension portion 36 so that disk 28 fits relatively closely and/or snugly against body portion 34. A bead or other formation of silicone or other friction-increasing or adhesive substance may be placed in indentations 37 of receiver member 22, to assist in maintaining disk 28 connected to receiver member 22. Disk 28, when configured in this way and fitted to receiver member 22, is substantially not rotatable with respect to receiver member 22 due to the fit between body portion 34 and opening 74, and potentially between extension portion 36 and hole 70. On a second side 75 of disk 28, roughening or other surface features intended for or amenable to making secure connections may be placed. In one particular embodiment, a set of radial splines or ridges 76 extend from hole 70 to an outer edge of disk 28.

A disk 30 associated with grommet member 24 may be provided in addition to or alternatively to disk 28. Disk 30 in the illustrated embodiment includes a hole 79 of approximately the same size and shape as body portion 50 of grommet member 24, so that body portion 50 can be inserted into or through hole 79. Stops, bosses or other extensions, such as protrusions 55, can be provided on grommet member 24 so that its connection to disk 30 is maintained. Similar to disk 28 and receiver member 22, in a particular embodiment hole 79 and body portion 50 may be keyed together or may both have a similarly dimensioned square, rectangular, polygonal, rounded, tapered or other shape to ease the fitting together of grommet member 24 and disk 30, and/or to limit or prevent rotation with respect to each other. As with the connection between disk 28 and receiver member 22, the connection between disk 30 and grommet member 24 can be enhanced by placing a bead or other formation of silicone or other friction-increasing or adhesive substance between disk 30 and grommet member 24. On one side 81 of disk 30, a channel or groove 82 is provided, and in one embodiment channel 82 may have a portion of approximately the same diameter as a portion of a bone fixation member (e.g. shank 25) extending through passage 54 in grommet member 24, or it may have a V-shaped cross-section or other configuration. A second side 83 of disk 30 may be roughened or include other surface features intended for or amenable to making secure connections, such as with a series of radial ridges or splines 84. In embodiments in which both disks 28 and 30 are used and have splines 76 and 84, respectively, splines 84 of disk 30 can engage with splines 76 disk 28, to prevent relative rotation of disks 28 and 30 with respect to each other when their respective roughened or splined sides are engaged.

It is preferred, but not necessary, that the structure of connector 20 be assembled prior to use in orthopedic surgery so that connector 20 may be quickly and easily implanted. Accordingly, in the embodiment in which disks 28 and 30 are used, disk 28 is fitted around extension portion 36 of receiver member 22. If used, a bead of silicone can preferably be placed in one or more of indentations 37 or elsewhere between disk 28 and receiver member 22 prior to fitting disk 28 around receiver member 22. Disk 30 is connected either to disk 28, by engaging their respective roughened or splined sides, or to grommet member 24 by inserting body portion 50 into hole 79, to a point up to the position where disk 30 is stopped by protrusion(s) 55, if they are present. Again, if used, a bead of silicone can preferably be placed between disk 30 and grommet member 24 prior to fitting disk 30 around grommet member 24. Grommet member 24 is connected to receiver member 22 by inserting grommet portion 52 into hole 44 of receiver member 22. If disks 28 and/or 30 are used but not previously assembled to receiver member 22 and grommet member 24, then grommet portion 52 of grommet member 24 can be inserted through hole 79 of disk 30, through opening 74 of disk 28, and into hole 44 of receiver member 22. Fixing member 26 (e.g. clip or block) is inserted between the prongs 56 of grommet member 24. At this point, preferably receiver member 22 and grommet member 24 are rotatable with respect to each other around an axis of hole 44. That is, disks 28 and 30 are separable by a sufficient space to allow them to rotate with respect to each other. Disks 28 and 30 are not rotatable with respect to receiver member 22 and grommet member 24, respectively, in the illustrated embodiment, although it will be understood that variations of disks 28 and/or 30 that are rotatable with respect to receiver member 22 and grommet member 24 are contemplated. Thus, prior to implantation when disks 28 and 30 are spaced sufficiently, grommet member 24 (connected to disk 30) is rotatable with respect to receiver member 22 (connected to disk 28).

Connector 20 (whether with or without disks 28 and 30) is used to connect a fixation member (via shank 25 or similar structure) and a longitudinal member (e.g. rod R). For example, a pedicle screw or hook may be fixed in or on a vertebra. Connector 20 can be placed over a shank (e.g. shank 25) of the pedicle screw or hook, with the shank being inserted through passage 54 in grommet member 24. Connector 20 can then be pivoted around the axis of the shank, and receiver member 22 can be rotated with respect to grommet member 24, substantially around an axis of hole 44 of receiver member 22. A rod can be inserted through channel 38 of receiver member 22. Any final adjustments the surgeon desires, such as adjustment to the positions of vertebral bodies, part(s) of connector 20, or the longitudinal member or fixation member, may be made.

A locking member, such as set screw 43, is then inserted into at least one of holes 40, 42 in receiver member 22. If the locking member is set screw 43 and at least one of holes 40, 42 is threaded, then set screw 43 is threaded into one of holes 40, 42. It will be understood that a second locking member (e.g. a second set screw) may be inserted into the other of holes 40, 42 for redundancy, but a single locking member in one of holes 40, 42 is believed to be sufficient to lock connector 20. Set screw 43 or other appropriate locking member presses the rod toward disk 28, e.g. set screw 43 is threaded down on the rod within channel 38, and tends to press the rod toward disk 28. The rod contacts disk 28 in channel 70, thereby forcing disk 28 toward and against disk 30. The shank of the pedicle screw 25 or other bone attachment member that extends through passage 54 in grommet member 24 is then sandwiched between channel 82 in disk 30 and the wall of passage 54 through grommet member 24. Connector 20 is thus locked, and the rod and pedicle screw 25 or other bone attachment member are immobilized with respect to each other.

Figure 4:
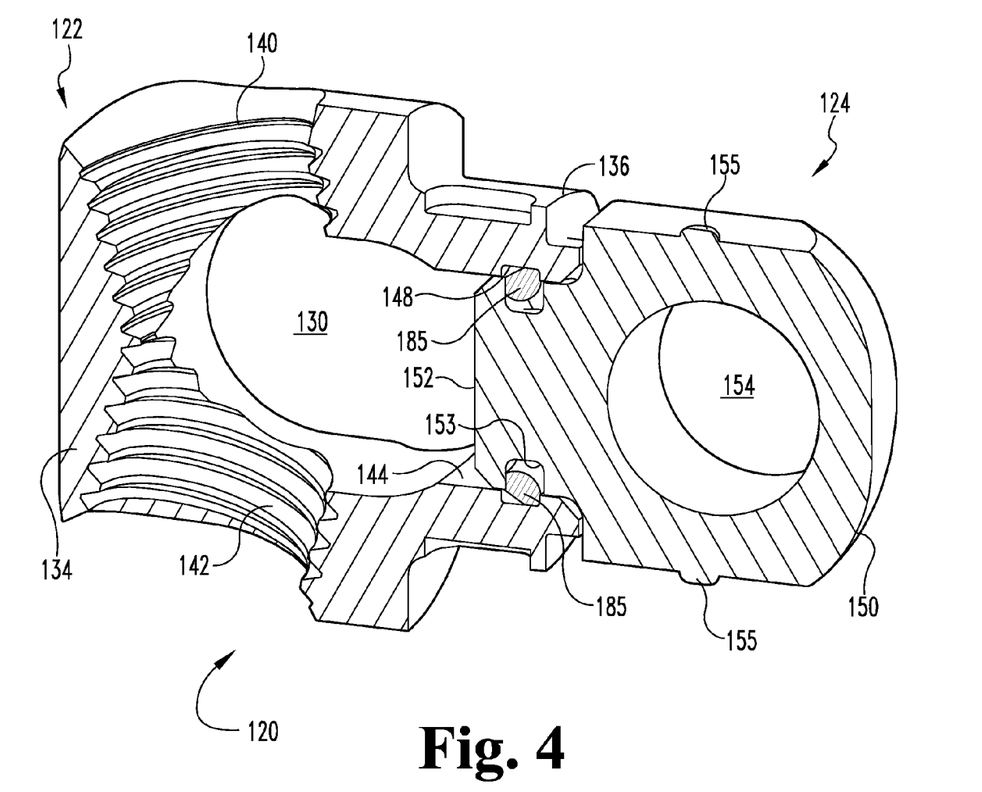
FIG. 4 is a cross-sectional perspective view of another embodiment of an apparatus according to the present invention.
Figure 5:
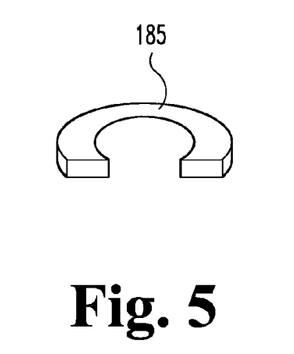
FIG. 5 is a perspective view of one embodiment of a retaining clip useful in connection with the embodiment shown in FIG. 4.
Figure 6:
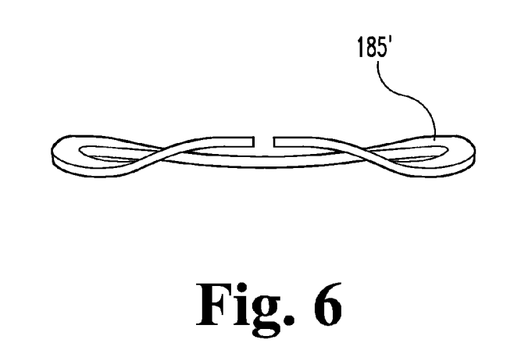
FIG. 6 is a side view of another embodiment of a retaining clip useful in connection with the embodiment shown in FIG. 4.

Referring now generally to FIGS. 4-6, another embodiment of a connector 120 is shown. Throughout the description that follows, items that are similar to previously-described items are denoted by a number with a changed or added initial digit. Connector 120 includes a receiver member 122 that is similar to receiver member 22 identified above. Specifically, receiver member 122 includes a body portion 134, an extension portion 136, indentations 137, an aperture 138 and holes 140, 142 and 144. On the inside of extension portion 136, a groove 148 is provided. Grommet member 124 includes a body portion 150, a grommet portion 152, a passage 154 and protrusions 155. In this embodiment, grommet portion 152 is substantially cylindrical, with the exception of a circumferential groove 153. Grommet portion 152 has an outer diameter slightly less than the inner diameter of hole 144 of receiver member 122.

A retaining ring 185 is also provided in this embodiment. In a specific embodiment, retaining ring 185 may be substantially C-shaped and expandable and/or compressible. Retaining ring 185 may be dimensioned to fit at least partially within a portion of groove 153 of grommet member 124 and groove 148 of receiver member 122, in one of an expanded, contracted or unstressed state. Thus, retaining ring 185 may have an unstressed outer diameter larger than the diameter of hole 144 but smaller than the diameter of groove 148 of receiver member 122, and an unstressed inner diameter less than the diameter of grommet portion 152 but greater than the diameter of groove 153 of grommet member 124. It will be appreciated that retaining ring 185 may be circular or of another shape, and may be made of a shape-memory material (such as the nickel-titanium alloy sold as NITINOL® or other alloys), or may be made of other sturdy biocompatible materials. As seen in FIG. 6, an alternative embodiment of retaining ring 185' is an undulating ring. Although not shown in FIG. 4, connector 120 may also include disks similar or identical to disks 28 and 30 described above.

Assembly and use of connector 120 is similar to that described above for connector 20. Grommet member 124 is connected to receiver member 122, through disks 28, 30 if they are used, by inserting grommet portion 152 into hole 144. Retaining ring 185 may be placed in groove 153 in grommet 124 prior to insertion. For example, if retaining ring 185 is a compressible C-shaped ring, it is compressed into groove 153 for insertion with extension portion 152 through hole 144. As another example, if retaining ring 185 is a shape-memory ring that expands when brought to or close to body temperature, it is placed in groove 153 in a compressed state for insertion with extension portion 152 through hole 144. When retaining ring 185 is adjacent groove 148 in receiver member 122, retaining ring 185 is allowed to expand through relief of compression stress or through a change of shape of a shape-memory material. Retaining ring 185 is at least partially within groove 153 and groove 148, limiting or preventing removal of grommet member 124 from receiver member 122. Grommet member 124 is rotatable with respect to receiver member 122, and connector 120 is locked by a set screw (e.g. set screw 43) or other locking member in essentially the same manner described above with respect to connector 20.

Figure 7:
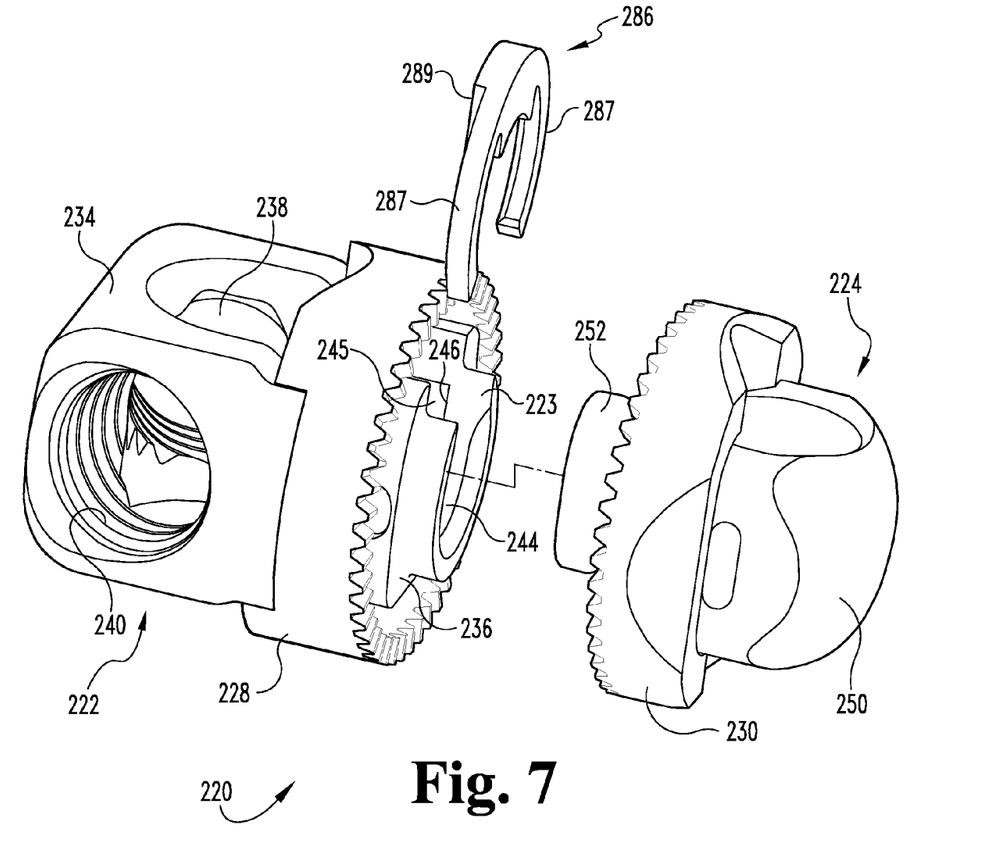
FIG. 7 is a partially exploded perspective view of another embodiment of an apparatus according to the present invention.
Figure 8:
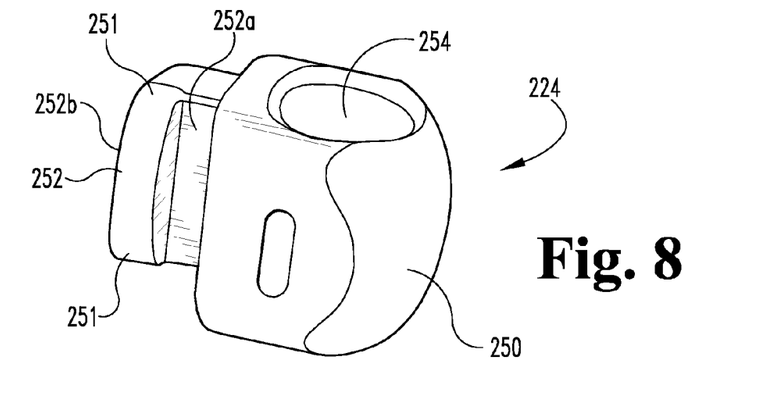
FIG. 8 is a perspective view of a member useful in the embodiment shown in FIG. 7.

Referring now generally to FIGS. 7-8, another embodiment of a connector 220 is shown. Connector 220 includes a receiver member 222 and a grommet member 224 (similar to grommet member 124), and in specific embodiments also includes disks 228 and 230. Disks 228 and 230, in the illustrated embodiment, are substantially identical to disks 28 and 30 described above. Receiver member 222 includes a body portion 234 that is substantially identical to body portion 34 of receiver member 22 described above. Extension portion 236 of receiver member 222 is generally C-shaped, having a gap 223 communicating with hole 244. Countersunk region 245 and ledge 246 are in extension portion 236. Grommet member 224 has a body portion 250 that is substantially identical to body portion 50 of grommet member 24. Extension portion 252 of grommet member 224 is in the general shape of a T-nut, having a narrow neck portion 252a and a laterally extended end portion 252b. End portion 252b includes outwardly extending bosses 251 on each side.

Also provided in this embodiment is a retaining clip 286 that is generally C-shaped, with arms 287 and a center protrusion 289. Protrusion 289 is generally sized and shaped to fit in part or all of gap 223 of receiver member 222, and arms 287 have an inner diameter equal to or slightly smaller than the outer diameter of extension portion 236 of receiver member 222.

As noted above with respect to connector 20, it is preferred, but not necessary, that the structure of connector 220 be assembled prior to use in orthopedic surgery. Accordingly, in the embodiment in which disks 228 and 230 are used, disk 228 is fitted around extension portion 236 of receiver member 222. Disk 230 is connected either to disk 228, by engaging their respective roughened sides, or to grommet member 224 by inserting body portion 250 into hole 280. Grommet member 224 is inserted into extension portion 236 of receiver member 222. This is accomplished by moving grommet member 224 away from a central axis of receiver member 222, so that end portion 252b of grommet member 224 is adjacent gap 253 in receiver member 222. Grommet member 224 is moved toward receiver member 222 so that extension portion 252 moves through gap 223, until end portion 252b is substantially above ledge 246 in receiver member 222. Grommet member 224 is then moved toward the central axis of receiver member 222, i.e. end portion 252b is "dropped in" to countersunk region 245 of receiver member 222. Clip 286 is then placed around extension portion 236 of receiver member 222, filling gap 253 with protrusion 289. In one embodiment, arms 287 are pressed against extension portion 236, so that arms 287 deflect apart. Additional pressure on clip 286 forces arms 287 around extension portion 236 until arms 287 fit around extension portion 236 and protrusion 289 enters gap 253. Preferably, there is significant friction between arms 287 of clip 286 and extension portion 236. Clip 286 thus inhibits or prevents removal of grommet member 224 from receiver member 222.

At this point, preferably receiver member 222 and grommet member 224 are rotatable with respect to each other, similar to connector 20 after receiver member 22 and grommet member 24 are connected. That is, disks 228 and 230 are separable by a sufficient space to allow them to rotate with respect to each other. Disks 228 and 230, in this particular illustrated embodiment, are not rotatable with respect to receiver member 222 and grommet member 224, respectively. Consequently, prior to implantation when disks 228 and 230 are spaced sufficiently, grommet member 224 (connected to disk 230) is rotatable with respect to receiver member 222 (connected to disk 228). Connector 220 is placed and locked with an elongated member and fixation member substantially as described above with respect to connector 220.

Figure 9:
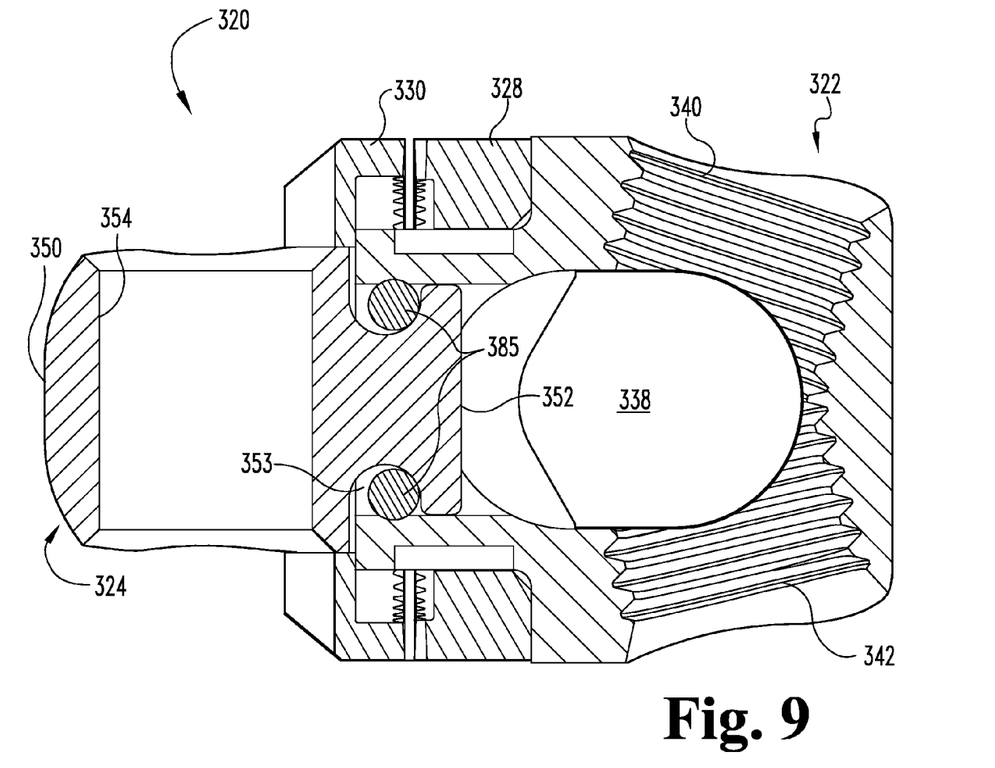
FIG. 9 is a cross-sectional view of another embodiment of an apparatus according to the present invention.
Figure 10:
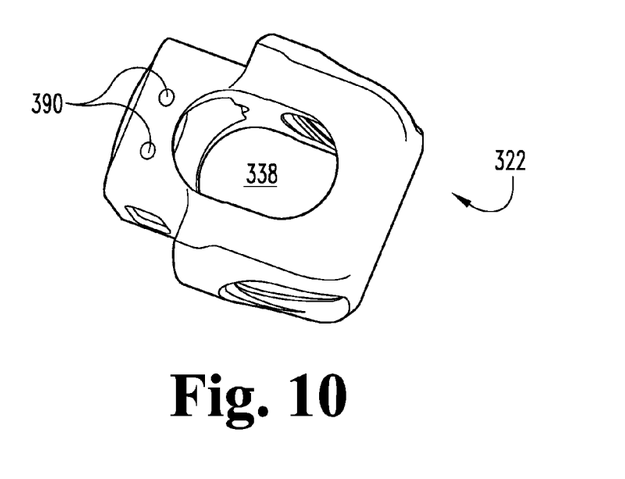
FIG. 10 is a perspective view of a member useful in the embodiment shown in FIG. 9.

A further alternative embodiment of a connector 320 is generally shown in FIGS. 9-10. Connector 320 is substantially identical to connector 120, with the exception that in place of retaining ring 185, retaining pins 385 are provided, as will be further described. Receiving member 322 is similar or identical to receiving member 122, having body portion 334, extension portion 336, opening 338, and holes 340, 342, 344, and further includes a pair of small holes 390 that are substantially parallel to channel 338 of receiver member 322. Grommet member 324 is similar or identical to grommet member 124, having an extension portion 352 with a groove 353. When grommet member 324 is inserted into hole 344 of receiver member 322, groove 353 in grommet member 324 substantially lines up with or overlaps at least a portion of holes 390 of receiver member 322. Pins 385 are then inserted into holes 390 so that at least a portion of pins 385 rest at least partially within groove 353 of grommet member 324. In this way, pins 385 prevent or hinder removal of grommet member 324 from receiver member 322. Holes 390 may be covered or partially filled with an adhesive or other substance or agent, such as a bead or other formation of silicone, to maintain pins 385 in place. Connector 320 is connected to an elongated member, for example a spinal rod, and a fixation member, such as bone screw 25, and locked substantially as described above.

Figure 11:
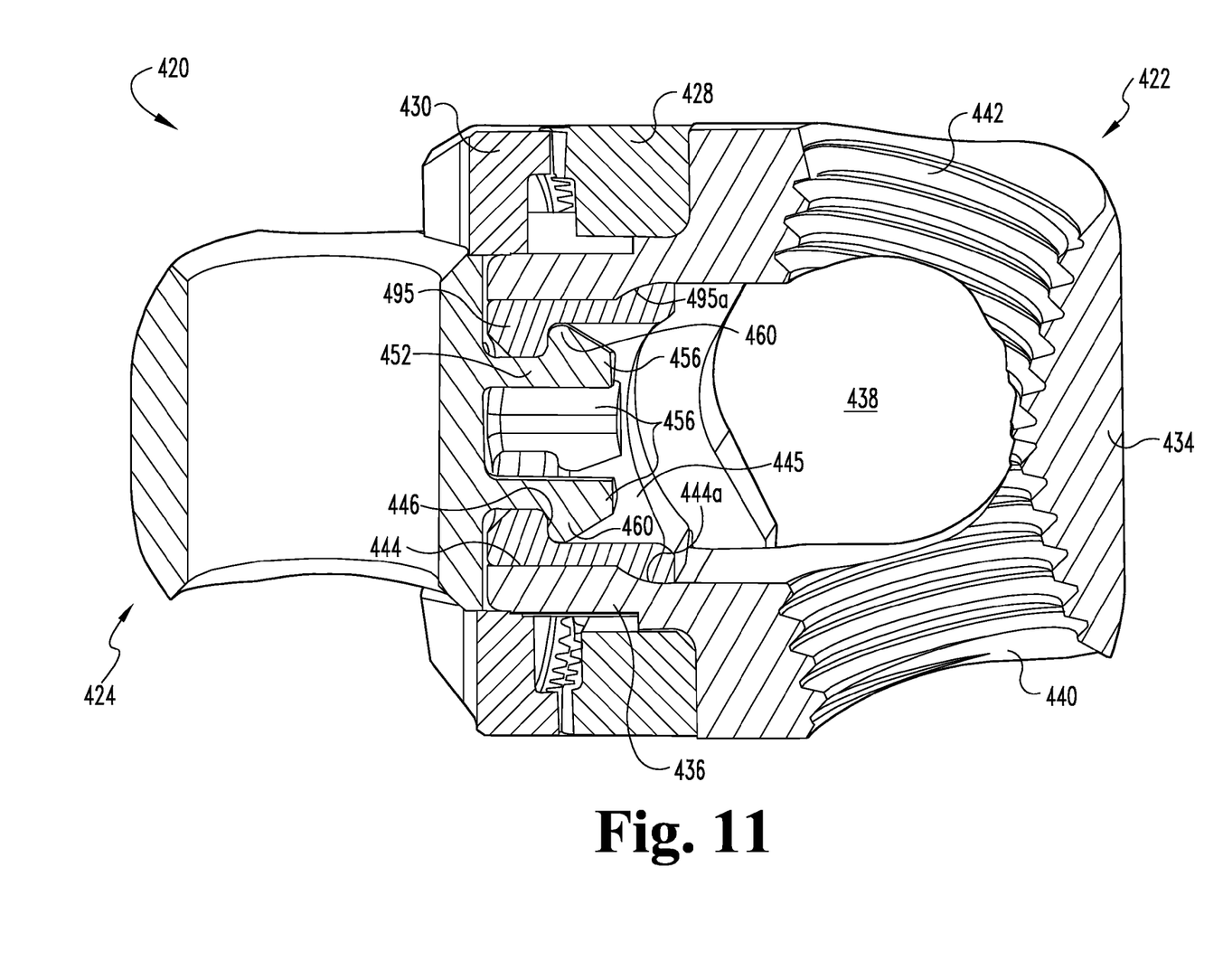
FIG. 11 is a cross-sectional view of another embodiment of an apparatus according to the present invention.

A further example of an embodiment of a connector 420 is generally shown in FIG. 11. Connector 420 is substantially identical to connector 20, with the exception that it includes an insert 495 that fits within receiving member 422. Receiving member 422 is similar or identical to receiving member 22, having body portion 434, extension portion 436, opening 438, and holes 440, 442, 444. Insert 495 includes a countersunk portion 445 and a ledge 446. In one particular embodiment, a curved surface 444*a* is provided in receiving member 422, and insert 495 has an outer surface 495*a* that is complementarily configured, so that insert 495 is retained within receiving member 422. It will be understood that conic, stepped, spring-biased or other configurations for insert 495 and/or surface 444*a* can be provided, or that portions of insert 495 or receiving member 422 can be made of shape-memory material to allow fitting together. Insert 495 may be substantially fixed relative to receiver member 422, or receiver member 422 and insert 495 may be rotatable and/or otherwise movable with respect to each other.

Grommet member 424 is similar or identical to grommet member 24, having an extension portion 452 and prongs 456. When grommet member 424 is inserted into hole 444 of receiver member 422 and insert 495, e.g. by squeezing together prongs 456 either by external pressure directly applied by an assembler, or by the action of hole 444 and/or insert 495 on flanges 460. Grommet member 424 resumes its unstressed form when flanges 460 move past ledge 446, e.g. prongs 456 of grommet member 424 snap into place with respect to insert 495 and receiver member 422. Grommet member 24 is then rotatably connected to insert 495 and/or receiver member 422. Further assembly and implantation of connector 420 is as described above with respect to other embodiments.

While one example of the use of connectors 20, 120, 220, 320, 420 described above is in the spinal field, it will be appreciated that the disclosed connectors can be used in a variety of orthopedic surgical procedures and/or with a variety of orthopedic surgical implants. Of course, any of connectors 20, 120, 220, 320, 420 can be sized or otherwise configured to be used in one or more parts of the spine (e.g. cervical, thoracic, lumbar or sacral), or with spinal implants such as intervertebral cages or spacers, rod connectors, bone plates, bone-growth promoting substances, or with other devices or therapeutic substances. The parts described herein are preferably made of biocompatible material such as stainless steel, titanium, certain hard plastics, shape-memory materials and/or other sturdy materials. Further, while individual embodiments of a connector have been described herein, it is understood that features, parts or aspects of one embodiment could be incorporated into another embodiment.

Additionally, while the implantation of connectors 20, 120, 220, 320, 420 has been described above as inserting an elongated member (e.g. a rod) into the connector after placing the connector over a fixation member (e.g. screw or hook), it will be appreciated that other methods can be used. For example, a surgeon may pre-fit one or more connectors 20, 120, 220, 320 and/or 420 to a rod, fixation member, or other spinal implant device before inserting such connectors into the body or placing such connectors on or with other implant devices. Thus, after fixation members are placed on or in the spine or at another surgical site, a rod with such pre-fitted connectors can be placed in the surgical site so that the pre-fitted connectors connect to respective fixation members. Similarly, such pre-fitted connectors could have fixation members pre-connected to them. Once the surgical site is properly prepared, the rod with pre-fitted connectors and fixation members can be introduced, with fixation members connected to vertebrae or other bones, appropriate adjustments made to bone, connectors, rod or fixation members, and the connectors locked when such adjustments are completed.

Any or all of the structures described herein can be provided in a sterile pack for providing necessary parts, or a variety of parts, to a surgeon. For example, one or more predetermined types or sizes of receiver member, grommet member, disks (if desired) and/or set screws may be provided in a single sterile package or kit. A surgeon can choose the sizes or types of structures he or she wishes to use during surgery. Alternatively, sterile kits containing a single predetermined size or type of receiver member, grommet member, disks (if desired) and/or set screws may be provided, so that waste of unneeded parts is limited or eliminated. Packages or kits of the structures described herein can also include or be provided with spinal rods, fixation members (e.g. screws, bolts, hooks, clamps, or the like), other connectors, instrumentation (e.g. rod benders, cutters, pushers, reducers or other rod handling tools; screwdrivers or other implanting tools; forceps, grippers or other holding tools; drills, bits, awls, reamers, guides, taps or other hole making tools; gauges or other measuring or sizing tools; or others) or other implants or devices useful in orthopedic surgery.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus comprising:
   a receiver member for holding a part of an elongated member, said receiver member having a channel therethrough extending along a longitudinal axis, at least one aperture extending along a closure axis for a closure member, and an opening extending transverse to said channel and said closure axis and through an external surface of said receiver member, wherein said closure axis is transverse to said longitudinal axis and said opening includes a reduced diameter portion adjacent to said external surface;
   a grommet member for holding a part of a bone implant member, said grommet member having a passage therethrough for the bone implant member and an extension transverse to said passage, said extension including two prongs which define a gap therebetween that is in direct communication with said passage; and
   a clip positioned between said two prongs, said clip including a pair of oppositely positioned lobes extending from a base portion and having a width equal to the gap between said two prongs such that pressure is applied to said two prongs to prevent compression of said two prongs,
   wherein said extension is inserted through said transverse opening of said receiver member so that said grommet member is non-threadedly and rotatably connected to said receiver member.

2. The apparatus of claim 1, wherein said at least two prongs each include a flange for interacting with a portion of said receiver member to retain said extension with said receiver member, wherein said receiver member includes an internal countersunk portion including a ledge defining said reduced diameter portion, wherein said flanges of said prongs are positioned adjacent said ledge.

3. The apparatus of claim 1, wherein said receiver member includes an internal countersunk portion including a ledge defining said reduced diameter portion.

4. The apparatus of claim 1, further comprising at least one intermediate member between said receiver member and said grommet member.

5. An apparatus comprising:
a receiver member for holding a part of an elongated member, said receiver member having a channel therethrough, at least one aperture extending obliquely to said channel for a closure member, and an opening transverse to said channel having an internal countersunk portion defining a ledge;
a grommet member for holding a part of a bone attachment member, said grommet member having a passage therethrough and at least two prongs extending transverse to said passage to an end positioned away from said passage, said prongs defining a gap therebetween which is in direct communication with said passage, said prongs being inserted into said transverse opening so that a portion of each of said prongs resides in said countersunk portion, whereby said grommet member and said receiver member are rotatably connected; and
at least one fixing member including a pair of oppositely positioned lobes extending perpendicularly from a base portion and extending between a first end oriented toward said end and a second end oriented toward passage, wherein when said prongs are positioned within said transverse opening said fixing member is lodged between two of said prongs and positioned between said end and said passage such that said first end of said at least one fixing member terminates at or before said end, said fixing member having a width equal to the gap between said prongs such that pressure is applied to said prongs to prevent compression of said prongs.

6. The apparatus of claim 5, further comprising first and second disks connected to one of said receiver member and said grommet member.

7. The apparatus of claim 5, wherein said fixing member is a clip configured to urge said prongs outward and retain said prongs within said receiver member.

8. A kit, comprising:
a sealed, sterile interior, said interior including a set of at least one receiver member of a predetermined size for holding a part of an elongated member, said receiver member having a channel therethrough, at least one aperture extending obliquely to said channel for a closure member, and an opening transverse to said channel;
a set of at least one grommet member of a predetermined size for holding a part of a bone implant member, said grommet member having a passage therethrough and a first extension and a second extension extending transverse to said passage to an end positioned away from said passage said first extension and said second extension defining a gap therebetween which is in direct communication with said passage; and
at least one fixing member extending between a first end oriented toward said end and a second end oriented toward said passage, said fixing member having a width equal to the gap between said first and second extensions such that pressure is applied to said first and second extensions to prevent compression of said first and second extensions,
wherein said first and second extensions are inserted through said transverse opening of said receiver member and said fixing member is positioned between said end and said passage so that said first end of said at least one fixing member terminates at or before said end and said fixing member engages with said first and extensions to retain said first and second extensions in said transverse opening and said grommet member is rotatably connected to said receiver member.

9. The kit of claim 8, further comprising a second set of at least one receiver member of a second predetermined size, and a second set of at least one grommet member of a second predetermined size.

10. The kit of claim 9, wherein said predetermined sizes are adapted for implantation in one or more of the set of spinal regions consisting of cervical, thoracic, lumbar and sacral.

11. The kit of claim 8, further comprising at least one instrument for implanting orthopedic bone implants.

12. The kit of claim 8, further comprising at least one additional bone implant.

13. The kit of claim 12, wherein said at least one additional bone implant is from the set consisting of intervertebral cages, intervertebral spacers, orthopedic rod connectors, bone plates, and bone-growth promoting substances.

14. An apparatus comprising:
a receiver member for holding a part of an elongated member, said receiver member having a channel therethrough, at least one aperture for a closure member, and an opening transverse to said channel;
a grommet member for holding a part of a bone implant member, said grommet member having a passage therethrough with a first configuration for receiving a bone implant member and an extension transverse to said passage, wherein said extension is formed by two prongs which include a gap therebetween with a second configuration directly communicating with said passage, wherein said prongs extend from a sidewall of said grommet member, said prongs being inserted through said transverse opening of said receiver member so that said grommet member is rotatably connected to said receiver member, and said second configuration preventing passage of said bone implant member through said space;
a clip positioned between said at least two prongs, said clip including a pair of oppositely positioned lobes extending perpendicularly from a base portion and having a width equal to the gap between said at least two prongs such that pressure is applied to said at least two prongs to prevent compression of said at least two prongs; and
at least one intermediate member between said receiver member and said grommet member, said intermediate member being substantially in the shape of a disk.

15. The apparatus of claim 14, wherein said intermediate member includes a roughened surface and said roughened surface includes a set of one or more splines.

16. The apparatus of claim 14, wherein said intermediate member includes a first surface having at least one opening for accommodating part of said receiver member so that said receiver member and said intermediate member are substantially not rotatable with respect to each other when said intermediate member is engaged with said receiver member.

17. The apparatus of claim 14, wherein said receiver member includes an extension portion defining said transverse opening and said intermediate member defines a hole through which said extension portion of said receiver member extends, and wherein said hole and said extension portion of said receiver member are matingly configured to substantially prevent relative rotational movement between said intermediate member and said receiver member.

* * * * *